United States Patent [19]

Kopf et al.

[11] 4,256,112
[45] Mar. 17, 1981

[54] HEAD POSITIONER

[75] Inventors: J. David Kopf, Tujunga; William Seiler, Jr., Van Nuys; Gerald S. Palecki, Burbank, all of Calif.; Howard H. Kaufman, Houston, Tex.

[73] Assignee: David Kopf Instruments, Tujunga, Calif.

[21] Appl. No.: 11,712

[22] Filed: Feb. 12, 1979

[51] Int. Cl.³ .................... A61B 17/00; G01N 21/00; G01N 23/00; A61G 13/00
[52] U.S. Cl. .............................. 128/303 B; 250/456; 250/491; 269/328
[58] Field of Search .................... 128/303 B, 752, 753, 128/754, 653, 777, 84 C, 87 B, 87 C, 97; 33/174 D; 250/456, 491; 269/328

[56] References Cited

U.S. PATENT DOCUMENTS

| 1,188,416 | 6/1916 | Dalbey | 33/174 D |
| 2,666,143 | 1/1954 | Thompson | 250/491 |
| 3,338,235 | 8/1967 | Gordon | 128/303 B |
| 3,542,030 | 11/1970 | Hoffman et al. | 128/303 B |
| 3,614,950 | 1/1971 | Rabey | 128/303 B |
| 3,737,660 | 6/1973 | Ando et al. | 250/456 |

FOREIGN PATENT DOCUMENTS 818711 of 1959 United Kingdom ................. 128/303 B

OTHER PUBLICATIONS

"The Neurosurgical Alleviation of Parkinsonism", Cooper, p. 14, 1956.
"Stereotoxic Apparatus & Operations in Russia in the 19th Century", Kandel et al., J. Neurosurg., vol. 37, Oct. 1972, pp. 407-411.
"Stereotoxic Computed Tomography", Bergström et al., Am J. Roentgenol 127: pp. 167-170, 1976.

Primary Examiner—Robert W. Michell
Assistant Examiner—C. W. Shedd
Attorney, Agent, or Firm—Bruce H. Johnsonbaugh

[57] ABSTRACT

A head positioner for radiologic and other medical procedures and a method for forming the head positioner are disclosed. A plastic rear component engages the backside of the patient's head, left and right plastic components engage each auditory meatus of the patient and a front component engages the nasion of the patient. Pressure is applied at the points of engagement and the components are secured to form a unitary headband structure. The headband is capable of repeated and periodic use in positioning the cranium of a human skull in precisely the same position relative to radiologic or other medical equipment. Apparatus for forming the headband structure is also disclosed.

5 Claims, 14 Drawing Figures

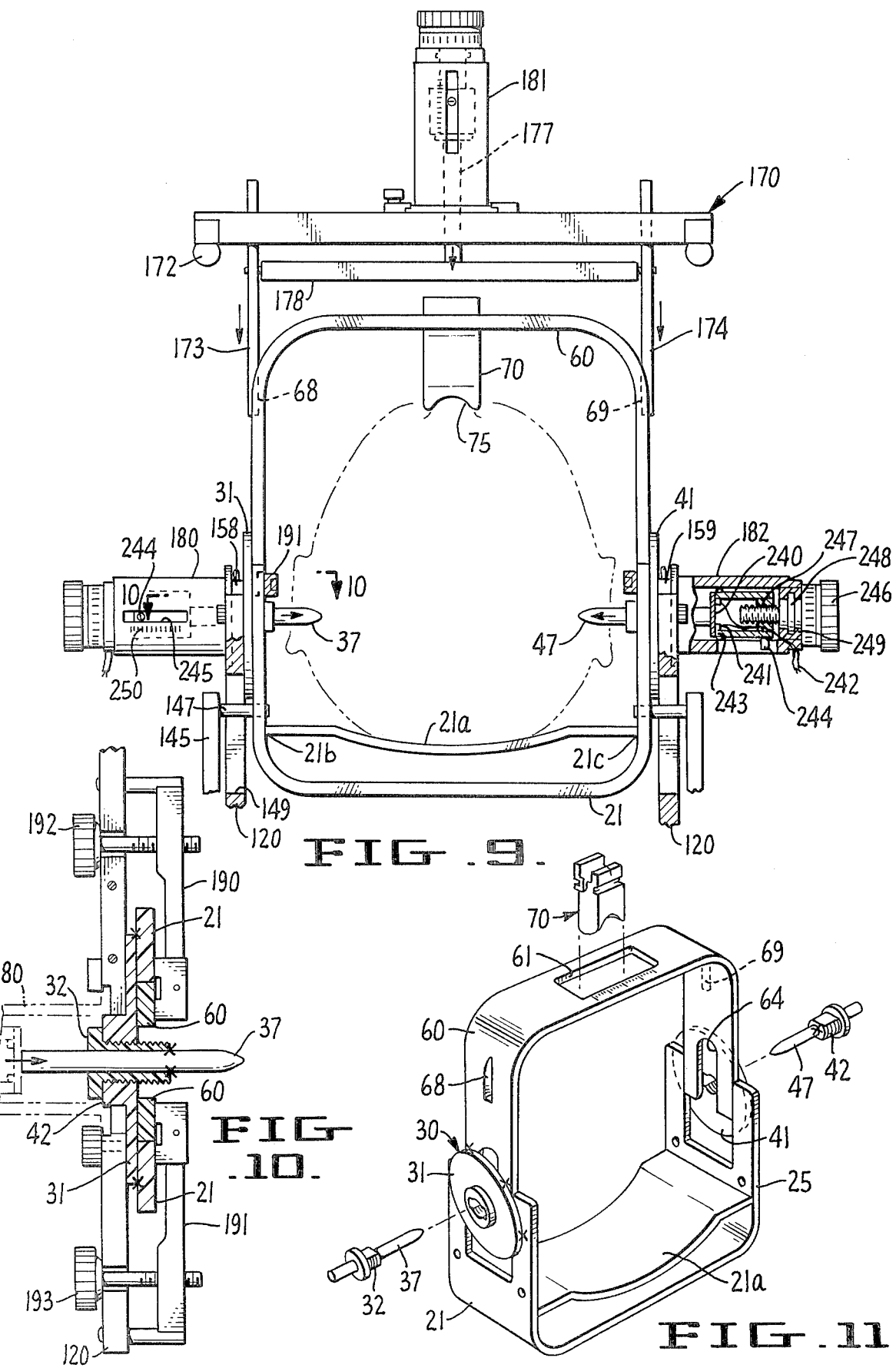

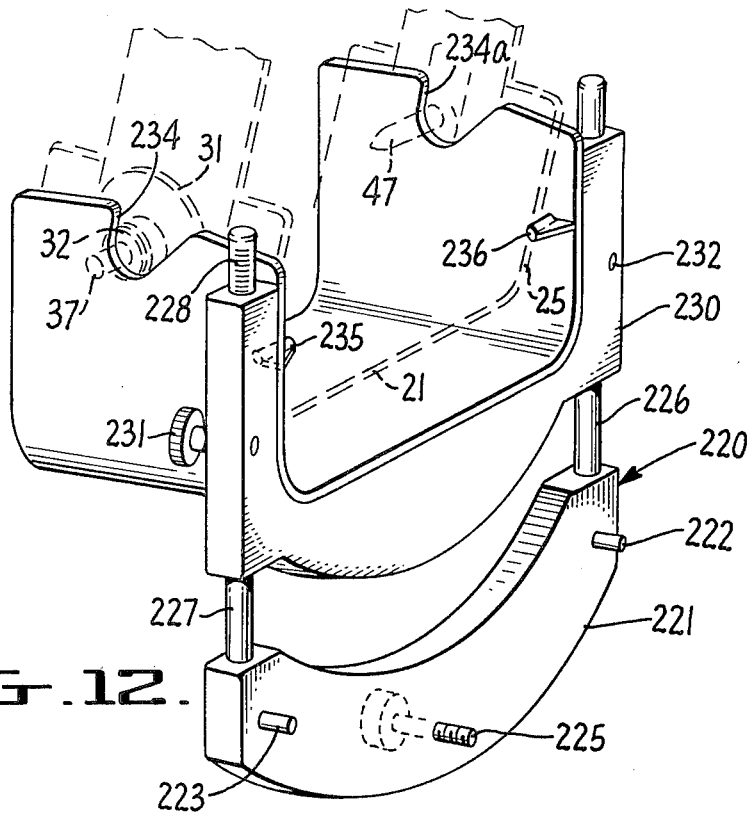
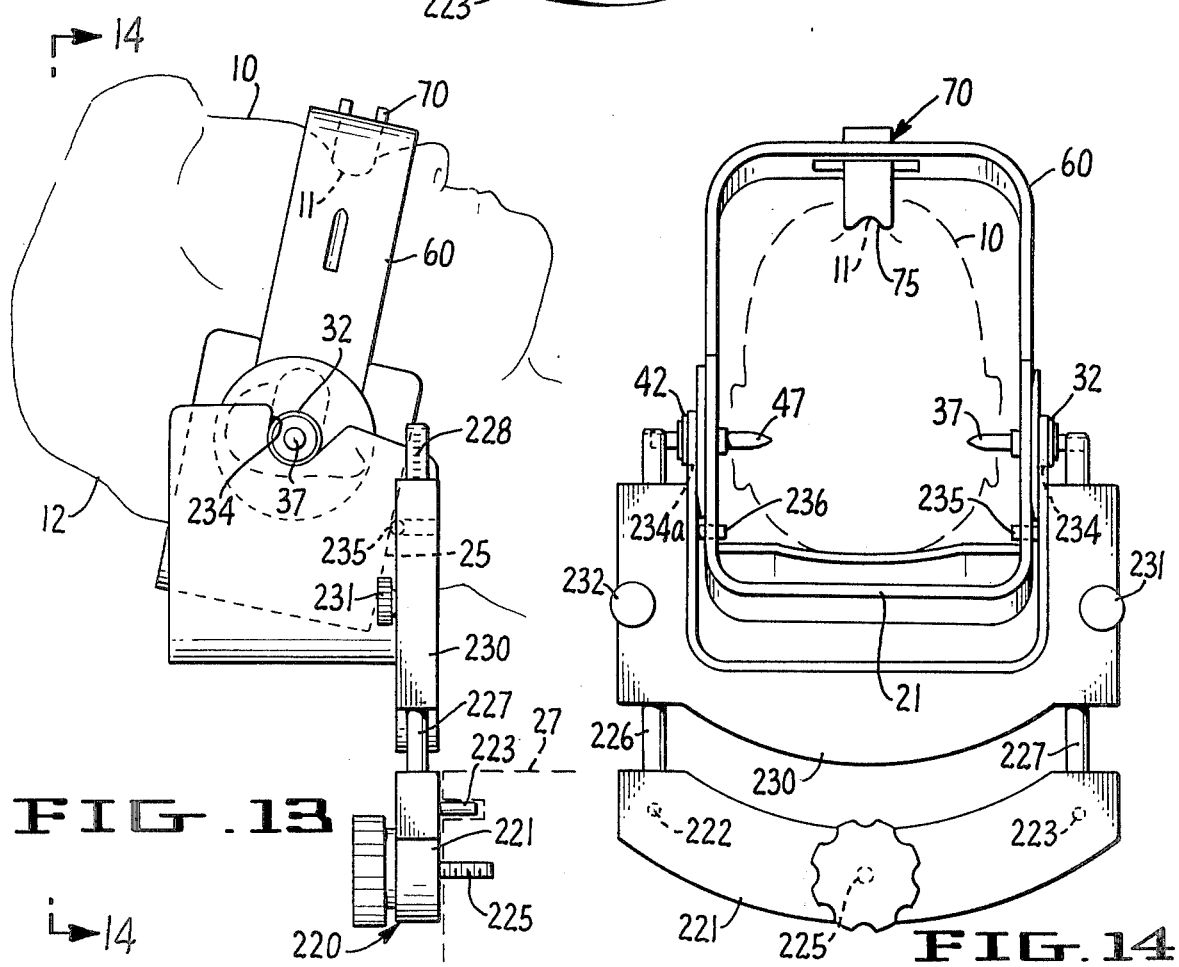

HEAD POSITIONER

This invention relates generally to stereotaxic instruments and more particularly to a human head positioner for use in radiologic and other medical procedures. The invention may be used in conjunction with diagnostic computed tomography, tumor biopsy, location of tumors precisely for radiotherapy, as well as other medical uses where precise positioning of the patient's skull is required.

The prior art includes an article entitled "Stereotaxic Computed Tomography" by Bergstrom and Greitz, published in the *American Journal of Roentgenology*, Volume 127, pp. 167-170 and dated 1976. This article discloses a plastic bandage fixed by adjustable aluminum hooks to a metal ring fitting the scanner opening. This device requires the insertion of screws into the calvarium. In contrast, the instant invention is non-invasive, does not cause excessive discomfort and trauma, and may be utilized without anesthesia.

A primary object of the invention is to provide a head positioner for repeated and periodic use in positioning the cranium in precisely the same position relative to radiologic or other medical equipment.

A further object of the invention is to provide a method for forming a headband for positioning the cranium for radiologic or other medical procedures.

Another object of the invention is to provide an apparatus for forming disposable headband positioners such that each specific patent will have his or her own head positioner custom fitted. Said apparatus has calibrated scales which correspond to calibrated scales on a mounting bracket attached to the radiologic or other medical equipment to assure that the patient is in the same relative position when the headband is formed and when the radiologic or other medical procedure is performed. The custom fitted head positioner is readily removed from the patient's head after being formed and may readily be reapplied to the patient's head repeatedly.

A further object of the invention is to provide a head positioner which is non-invasive, does not cause excessive discomfort or trauma, and which does not require the use of anesthesia.

Another object of the invention is to provide a head positioner which is applied with sufficient localized and carefully monitored pressure at the nasion and external auditory meatii to assure repeatable positioning while maintaining a comfortable fit for the patient.

Further objects and advantages of the invention will become apparent from the following description and from the drawings wherein:

FIG. 9 is an elevational view of a portion of the apparatus of FIG. 4 as the headband is being formed;

FIG. 10 is an elevational view in section along the line 10—10 of FIG. 9;

FIG. 11 is a perspective view of the reusable headband;

FIG. 12 is a perspective view of a portion of the invention;

FIG. 13 is an elevational view showing the head positioner in position, ready for a radiologic procedure; and FIG. 14 is an elevational view along the line 14—14 of FIG. 13.

Figure 1:
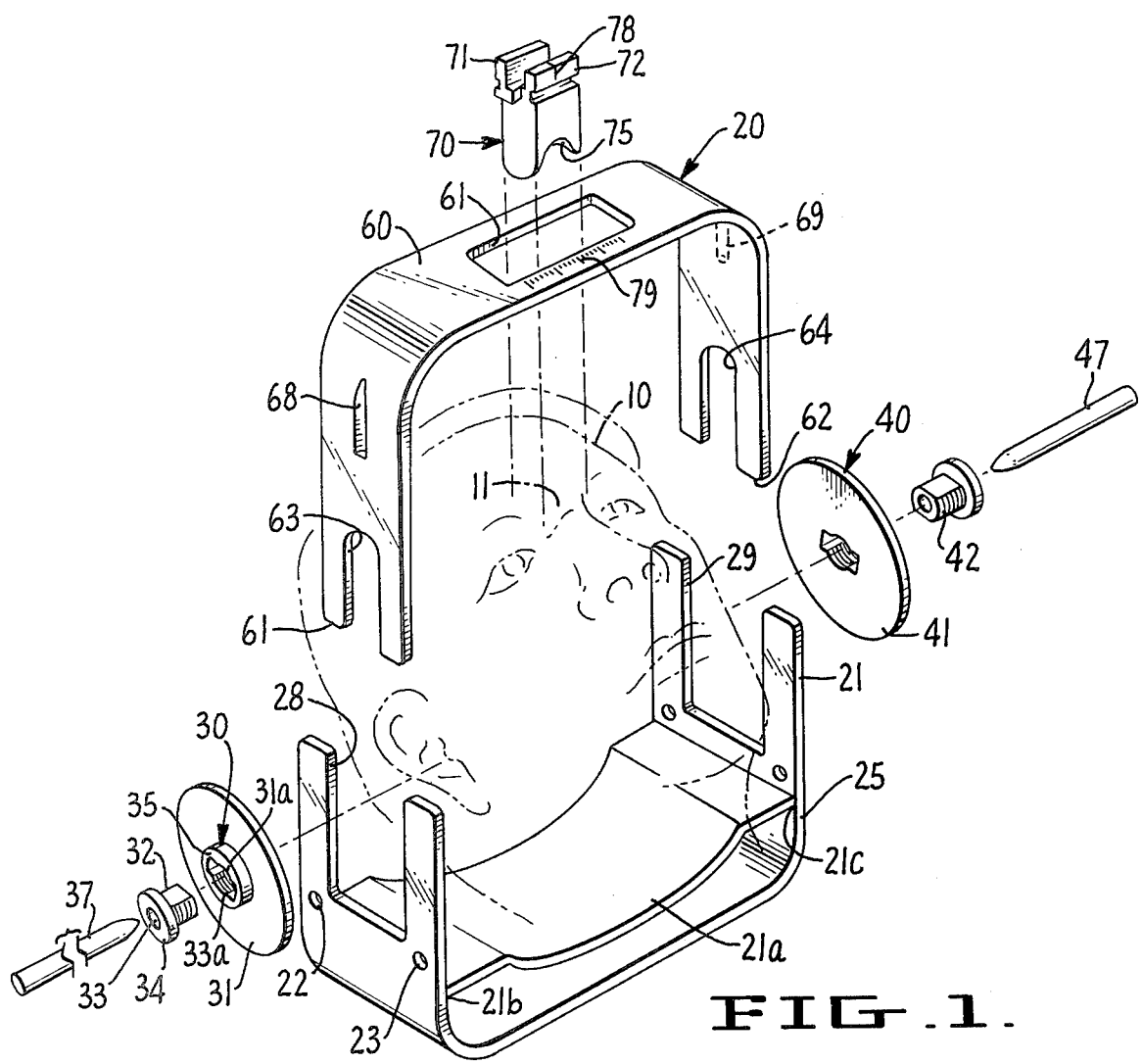
FIG. 1 is an exploded, perspective view of the disposable headband.

Referring to the drawings, FIG. 1 shows patient 10 in phantom and plastic headband generally as 20 in exploded fashion.

Figure 2:
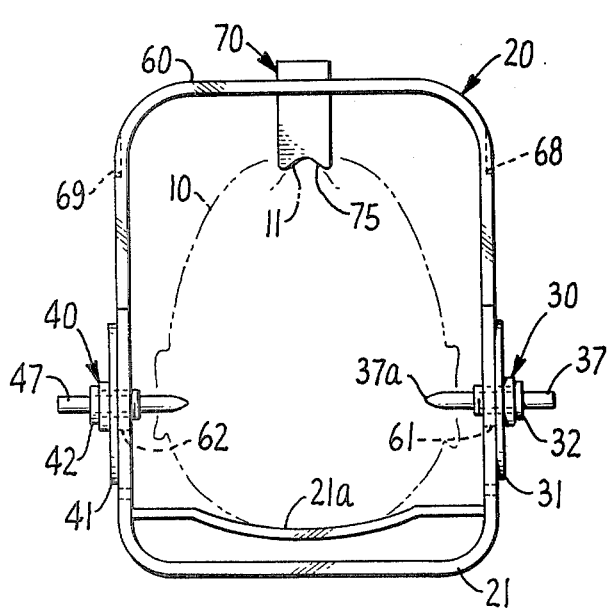
FIG. 2 is an elevational view of the headband in position on the patient's head.
Figure 3:
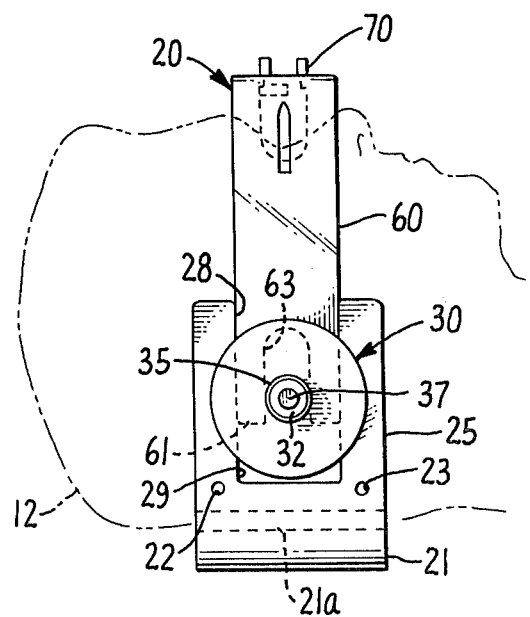
FIG. 3 is an elevational view of the headband of FIG. 2.
Figure 4:
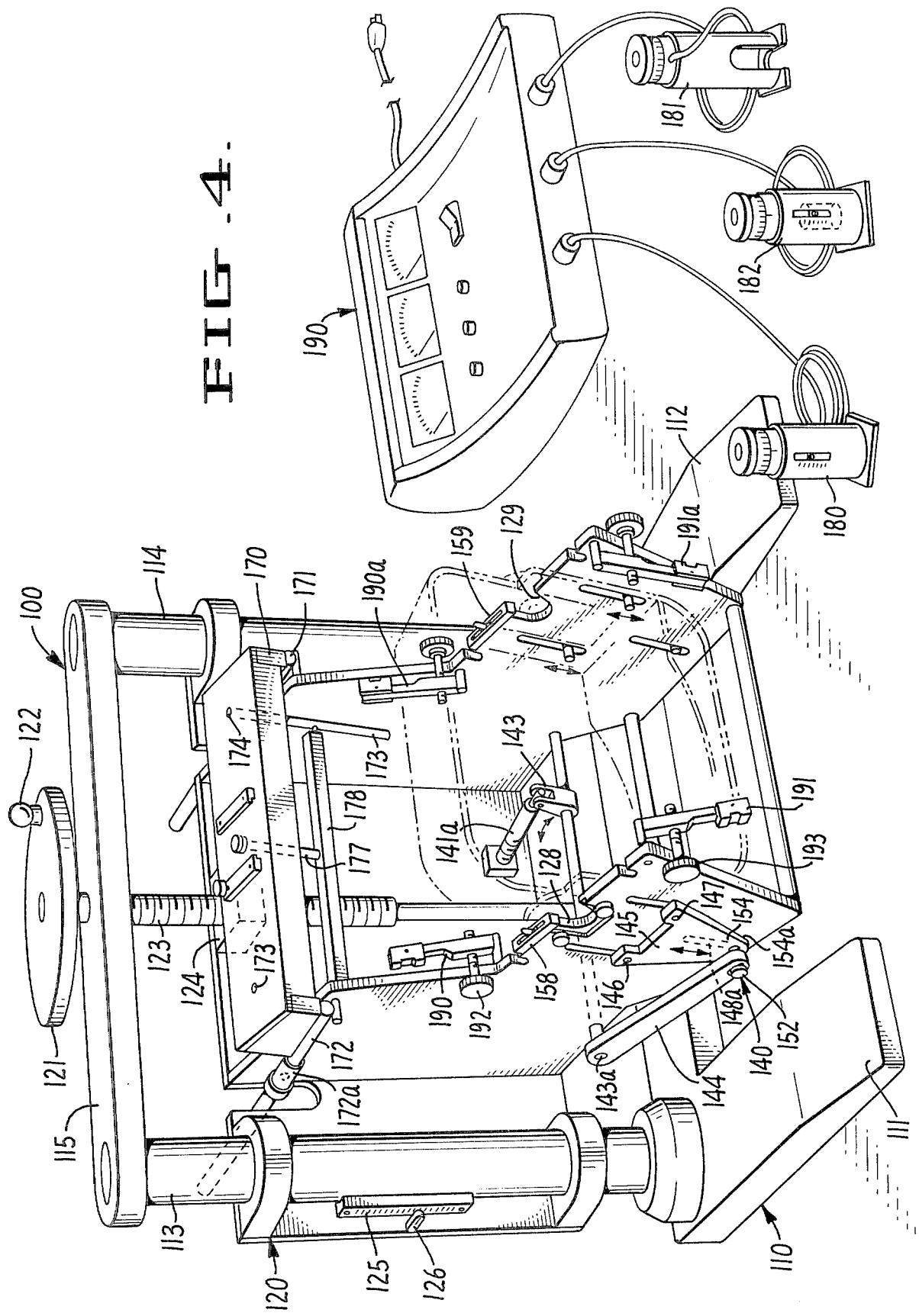
FIG. 4 is a perspective view of the apparatus for forming the headband shown in FIGS. 2-3.

One plastic band component 21 engages the head of patient 10 and extends at least partially around the backside of the head, as shown in FIG. 3. Member 21a extends from point 21b of band 21 to point 21c and provides comfortable support for the patient's head. Second and third band components or ear engagement means 30 and 40 engage the right and left external auditory meatus of the patient respectively. A fourth band component 60 engages the nasion 11 of the patient through nose bridge 70. Referring to FIGS. 1-3, means for engaging nasion 11 includes a connector, contact or nose bridge 70 which applies localized pressure to nasion 11. Nose bridge 70 is fitted into a rectangular recess 61 in the front component 60 of headband 20. As described in greater detail below, the components shown in FIG. 1 are secured together under pressure to form a custom-fitted, unitary headband (as shown in FIGS. 2 and 3) capable of repeated and periodic use in positioning the cranium 12 of patient 10 in precisely the same position relative to radiologic or other medical equipment, such as CT scanners and the like.

FIGS. 4, 5, 6, 9 and 10 show how the headband 20 of FIGS. 1-3 is formed. Apparatus 100 for forming headband 20 includes a frame 110. Frame 110 includes feet 111 and 112 which support vertical cylindrical rods 113 and 114, respectively. Cap 115 rigidly connects the tops of rods 113 and 114.

A vertically adjustable carriage 120 is carried by frame 110. Carriage 120 is driven vertically by crank 121 and handle 122. Crank 121 is rigidly connected to threaded shaft 123 which in turn threads into jack nut 124 on carriage 120. A scale 125 is rigidly affixed to rod 113. Indicator 126 on carriage 120 measures the elevation of carriage 120 relative to the bottom of the feet 111 of frame 110. Recesses 128 and 129 of carriage 120 receive the ear engagement means 30 and 40, respectively, as described in greater detail below. Recesses 128 and 129 are at an elevation above the base of feet 111 of frame 110 as reflected by the position of indicator 126 in relation to scale 125.

Figure 5:
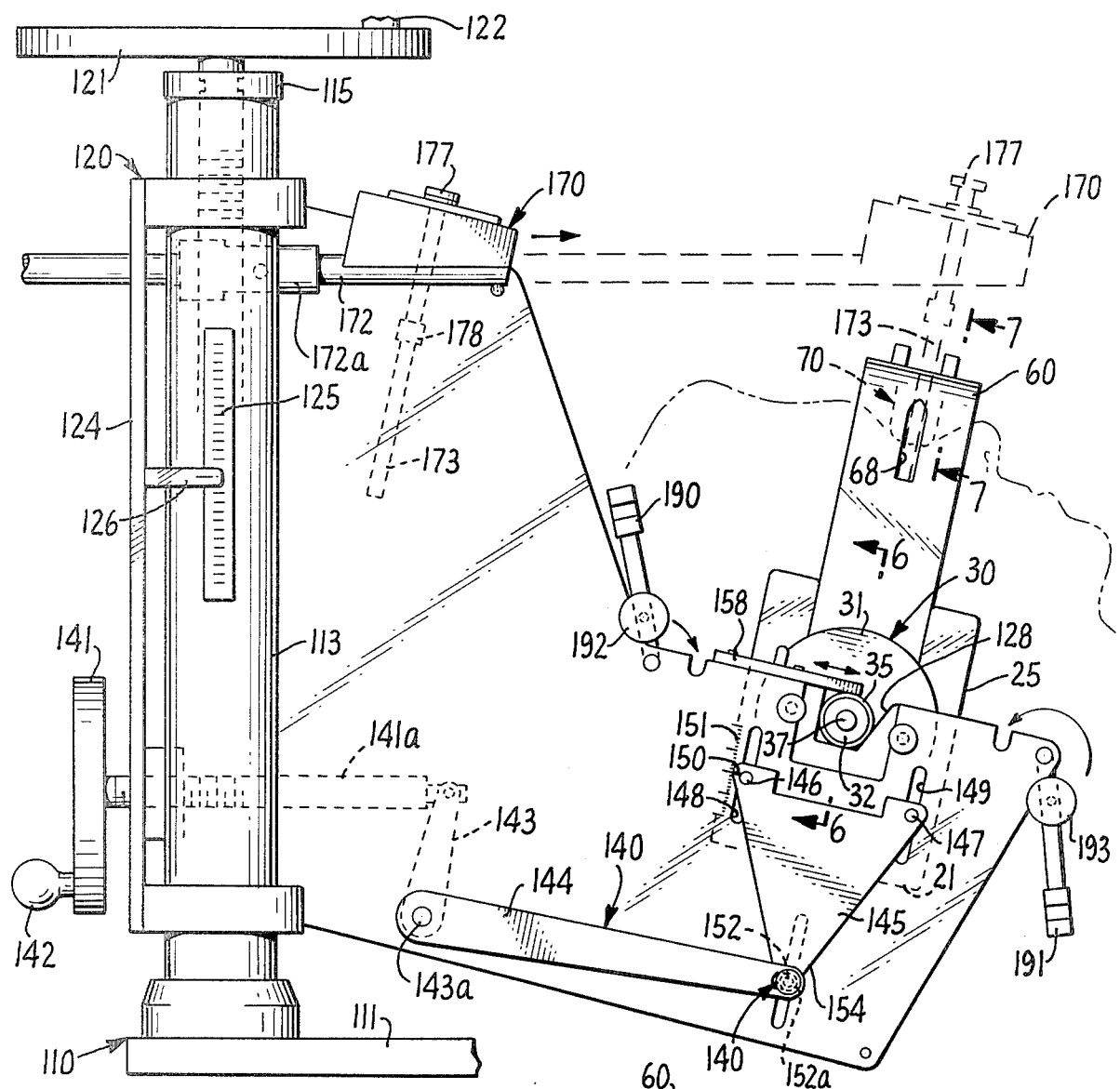
FIG. 5 is an elevational view of the device of FIG. 4.

Adjustable lower support means 140 raises or lowers the patient's head as shown best in FIG. 5 so that the patient's ear canals are aligned with ear engagement means 30 and 40. Hand crank 141 driven by handle 142 operates linkage arms 143 and 144 via threaded shaft 141a connected to crank 141 and shaft 143a which carries linkage arm 144. In response to rotation of crank 141, triangular piece 145 is raised or lowered. Similar linkage arms and triangular piece are located on the opposite side of apparatus 100 from that shown in FIG. 5. Triangular piece 145 carries pins 146 and 147 which ride in vertical slots 148 and 149 formed in carriage 120.

An indicator 150 carried at the top of triangular piece 145 is read against scale 151 on recess 148. The effect of rotating crank 141 is to either raise or lower pins 146 and 147 which in turn raises or lowers the head of the patient as described below. Pin 152 has a diameter of ¼ inch and is pressed into the lower portion of triangular piece 145. Pin 152 extends through a recess 152a in linkage arm 144. Recess 152a is 5/16 inch high and ½ inch wide. Pin 152 rides in a vertical recess 148a in carriage 120 similar to recesses 148 and 149. The lower portion 154a of triangular piece 145 is tapered so that the top end of triangular piece 145 may rotate in a direction outwardly of the paper in FIG. 5 (also see FIG. 6). This feature facilitates the pressing of plastic component 21 into position in carriage 120 by deflecting pins 146 and 147 momentarily until recesses 22 and 23 (see FIG. 1) are in position to receive the ends of pins 146 and 147.

To form the head positioner, the lower head support band 21 is pressed downwardly into position in carriage 120 such that recesses 22 and 23 are engaged by pins 146 and 147.

Next, the hub portions 31 and 41 of ear engagement means 30 and 40 with their respective bolts 32 and 42 threaded into place are placed in recesses 128 and 129 and latches 158 and 159 are slid forward to the position shown in FIG. 5 to restrict any upward motion of hubs 31 and 41. Hub 31 has interrupted helical threads 31a on its center bore 33a, as shown best in FIG. 1. Plastic bolt 32 has a cylindrical recess 33 formed along its longitudinal center and has interrupted helical threads which mate with the interrupted helical threads of hub 31. Bolt 32 is inserted into the bore 33a in the center of hub 31 and may be pushed into hub 31 until its head 34 seats against the outermost portion 35 of hub 31. As a practical matter, bolt 32 is inserted nearly until head 34 seats and is then rotated clockwise, so that the interrupted threads of bolt 32 engage the interrupted threads of hub 31, and head 34 seats firmly against the outermost portion 35 of hub 31 as the helical threads advance the bolt 32 home.

The patient then places the back of his head in position on lower head support band 21a (FIG. 5). By operation of the adjustable lower support means 140, the patient's head is raised or lowered until the ear canals are aligned with the center of disc-shaped hubs 31 and 41 of ear engagement means 30 and 40.

Figure 6:
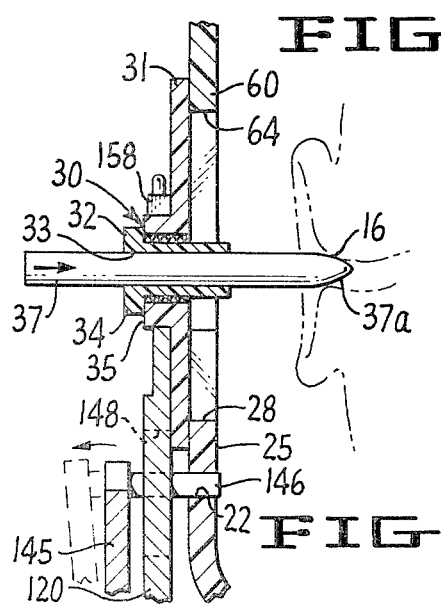
FIG. 6 is an elevational view in section along the lines 6—6 of FIG. 5.

At this point, the ear bars 37 and 47 are loosely inserted into position as shown best in FIG. 6. Ear bar 37 has a tapered tip 37a which is inserted or slid into the recess 33 of bolt 32 and pressed against the external auditory meatus 16 of the patient as described below. Ear bar 37 will subsequently be rigidly cemented to bolt 32. After cementing, ear bar 37 and bolt 32 are removed from the patient's ear canal and contact with the external auditory meatus by rotating bolt 32 in a counterclockwise position until the interrupted threads no longer mate, at which point ear bar 37 and bolt 32 slide freely out of the plastic frame and away from the patient.

Figure 8:
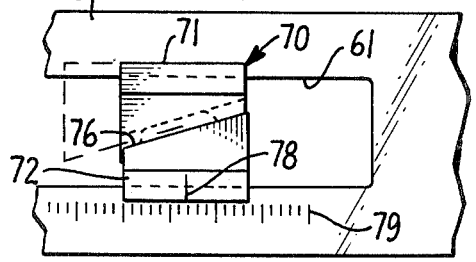
FIG. 8 is a plan view of a portion of the device along the lines 8—8 of FIG. 7.
Figure 7:
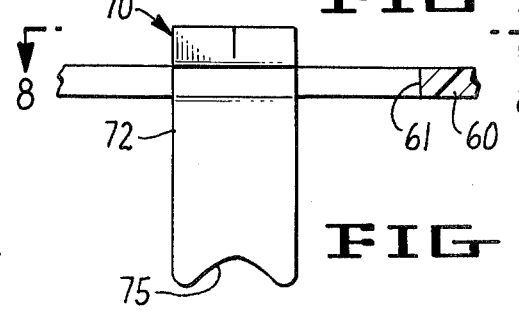
FIG. 7 is an elevational view along the line 7—7 of FIG. 5.

Once the right and left bars 37 and 47 have been placed loosely into the patient's ear canals, upper support band 60 is placed loosely into position, as shown in FIG. 5. The lowermost portions 61 and 62 of upper support band 60 slide into recesses 28 and 29 of lower head support band 21. Recesses 63 and 64 are provided in upper support band 60 to provide clearance for ear bars 37 and 47. Nasion engagement means 70 is then inserted loosely into rectangular recess 61 in upper support band 60 as shown in FIGS. 7 and 8. Nasion engagement means or nose bridge 70 comprises two plastic components 71 and 72 (see FIG. 1). Component 72 has at its lowermost extreme a curved recess 75 which is designed to accommodate the nasion or bridge of the nose of the patient. Nose bridge component 71 and the upper portion of component 72 are wedge-shaped and separated along a diagonal boundary 76 and, as shown in FIG. 8, if component 71 were moved to the right relative to component 72, nose bridge 70 would exert greater force against the sides of recess 61. Conversely, if piece 71 were moved to the left to the position shown in phantom, nose bridge 70 could be easily removed from recess 61. As shown in FIG. 5, nasion engagement means 70 is in proper alignment with the nasion 11 of the patient. Typically, the nasion engagement means 70 is out of alignment when upper support band is slid into position, either by being displaced toward the tip of the patient's nose or toward the patient's forehead. To correctly align the nasion 11 with nasion engagement means 70, crank 121 is rotated which moves carriage 120 vertically, thereby rotating the patient's head about the axis of his shoulders, thereby aligning the patient's nasion 11 with nasion engagement means 70. Nose bridge 70 is laterally positioned over the patient's nasion 11 by sliding it to the left or right as shown in FIG. 8. Indicator 78 on nose bridge 70 is read against scale 79 on upper support band 60 for use in future application to the patient. Nose bridge 70 is then firmly pressed into engagement with the sides of recess 61.

Next, cross beam 170 is pulled from its position shown in FIG. 5 upwardly and outwardly to a position directly above upper support band 60 as shown in phantom in FIG. 5. Cross beam 170 is carried by telescoping arms 171 and 172 which are hingedly connected to carriage 120 as by hinge 172a. Locating pins 173 and 174 are carried by cross beam 170 and are lowered into vertical grooves 68 and 69 formed in upper support band 60 as shown in FIG. 9.

Cross beam 170 is lowered so that locating pins 173 and 174 carried rigidly in cross beam 170 slide into grooves 68 and 69 in upper support band 60. A cross bar 178 connects pins 173 and 174.

The patient is now ready to have the plastic components formed into a unitary head positioner. Load cells 180, 181 and 182 are mounted in the position shown in FIG. 9.

Each of these load cells has a transducer membrane 240 which carries a plurality of strain gauges 241. Strain gauges 241 read out total force applied by transducer diaphragm 240 through leads 242 which connect to console 190 shown in FIG. 4. Transducer membrane 240 is carried at the end of cup member 243. Cup member 243 has a pin 244 extending through a recess 245 in the external housing of each load cell. The effect of pin 244 is to prevent the rotation of cup member 243 and transducer diaphragm 240. A knurled vernier knob 246 drives a threaded shaft 247 which threadably engages cup 243 so that as vernier knob 246 is rotated, transducer diaphragm 240 may either by urged against ear bar 47 or withdrawn from engagement with ear bar 47. Bearing 249 carries flange 248 to prevent longitudinal movement of threaded shaft 247. The pin 244 also indicates the longitudinal position of transducer diaphragm 240. A scale 250 is provided on the exterior of each load cell for this purpose. It is understood that each of the load cells is constructed in the same manner. Load cell 182 in FIG. 9 is shown rotated 90° from the position of load cell 180 for purposes of illustration.

Load cell 180 applies a force to ear bar 37, and load cell 182 applies a force to ear bar 47. The recommended force settings applied to ear bars 37 and 47 are 0.6 pounds. The electronic console 190 is provided with scales reflecting the force applied to ear bars 37 and 47 and also provides an audio alarm for any overloading of the load cells. In addition, a balancing circuit is provided which illuminates a green light if the force on each ear is approximately the same, but which illuminates a read light if the forces on each ear are out of balance. Similarly, load cell 181 applies a force to nose bridge 70 through a pin 177 and cross bar 178. The recommended force on the nose bridge is 1.0 pounds. As the force is applied to nose bridge 70, flexion of upper support band 60 is induced by the presence of pins 173 and 174 in recesses 68 and 69. Introduction of flexion minimizes any relaxation of support band 60 after the plastic components are all cemented together and the load cells are removed.

When the appropriate forces are applied, clamps 190 and 191 (FIG. 10) are placed in position and are drawn snug by knurled headband clamping bolts 192 and 193. FIG. 10 shows two clamps applied on the left ear engagement means. Similar clamps are also applied on the right ear engagement means. The effect of clamps 190 and 191 is to secure hub 31 to upper support band 60 and lower support band 21. A quick-setting cyanoacrylate adhesive is then applied at the places marked "X" of FIGS. 10 and 11 and at similar positions relative to hub 41, to rigidly secure hub 31, upper support band 60 and lower support band 21 and hub 41 into a unitary assembled headband as shown in FIG. 11. Each bar 47 is cemented to bolt 42 as shown in FIG. 11 and each bar 37 is cemented to bolt 32 as shown in FIGS. 10 and 11.

Once the cement has dried, the patient may be removed from the headband forming apparatus 100 with the unitary headband in position on his head by loosening load cells 180, 181 and 182 and removing them from their mounting brackets, lifting and retracting cross seam 170; releasing the four clamps 190, 190a, 191 and 191a; and sliding latches 158 and 159 to the rear. The patient may now sit up and go directly to the CT scanner, for example.

Alternatively, the assembled unitary headband may be removed, preferably with the patient lying down, by rotating ear bars 37 and 47 counterclockwise so that their respective interrupted threads are disengaged and they slide freely away from the patient. The nose bridge 70 is next removed by sliding its respective components in a direction to release nose bridge 70 from recess 61.

FIGS. 12, 13 and 14 show the mounting means 220 of this invention. Table mounting bracket 221 has mounting pins 222 and 223 which are inserted into recesses in the patient table 27 for a CT scanner, for example. Threaded shaft 225 is threaded into a recess in table 27 and mounting bracket 221 is fastened fastened securely to table 27. Bracket 221 carries vertical pins 226 and 227. Pin 227 has a scale 228 which corresponds to the scale 125 of frame 110. Before the patient is placed on scanning table 27, the upper mounting bracket 230 is raised to a position such that the reading of scale 228 is the same as the reading on scale 125 when the unitary headband was formed. Bracket 230 is secured into position by rotation of threaded bolts 231 and 232. The patient is then placed into position with the unitary head positioner resting in bracket 230. Bolt 32 of ear engagement means 30 rests in recess 234 of bracket 230. Bolt 42 of ear engagement means 30 is positioned in recess 234a of bracket 230. The forward edge 25 of lower support band 21 is urged against retaining pins 235 and 236. As shown in FIG. 12, alignment means include recesses 234 and 234a, scale 228 and pins 235 and 236. With the patient in the position shown in FIGS. 13 and 14, his head is at the precise elevation that is was at when the integral headband unit was formed. In addition, each time the patient is placed in the integral headband and on the mounting means 220, his cranium is in precisely the same position as on the previous occasion. As shown best in FIG. 13, the patient's cranium is fully exposed for radiologic procedures. The headframe and that portion of mounting means 220 beneath the headframe are plastic and minimize interference with CT scans and other radiologic procedures.

What is claimed is:

1. A headband for use in repeatably positioning a patient's cranium in precisely the same position relative to medical equipment, said headband comprising:
   a front component having a contact for engaging the nasion of a patient with localized pressure, a rear component engageable with the back side of the head,
   means including left and right components interconnecting said front and rear components, and means removably supported in said right and left components for engaging the left and right external auditory meatus of the patient with localized pressure,
   wherein said left and right components are disc-shaped hubs with interrupted threads on their center bores and wherein said means removably supported in each of said right and left components comprise:
   a bolt with interrupted helical threads and a cylindrical recess extending along its longitudinal center, and
   an ear bar slidably carried by said recess having a tapered tip for engaging the external auditory meatus.

2. A headband for use in repeatably positioning a patient's cranium in precisely the same position relative to medical equipment, said headband comprising:
   a front component having a contact for engaging the nasion of a patient with localized pressure, a rear component engageable with the back side of the head,
   means including left and right components interconnecting said front and rear components, and means removably supported in said right and left components for engaging the left and right external auditory meatus of the patient with localized pressure,
   wherein said front component comprises an upper support band extending across the front of the patient's head and having a rectangular recess formed therein above the patient's nasion and wherein said contact for engaging the nasion comprises two wedge-shaped components removably carried by said rectangular recess.

3. A headband for use in repeatably positioning a patient's cranium in precisely the same position relative to medical equipment, said headband comprising:
   a front component having a contact for engaging the nasion of a patient with localized pressure, a rear component engageable with the back side of the head, means including left and right components interconnecting said front and rear components, and means removably supported in said right and left components for engaging the left and right external auditory meatus of the patient with localized pressure, wherein said front component slidably engages said rear component to facilitate adhesive cementing of the components.

4. The headband described in claim 8 further comprising in combination an apparatus for initially forming said headband, which apparatus is capable of repeated use for positioning said headband and thereby the cranium of a human skull in precisely the same position relative to medical equipment, said comprising:
 a frame,
 a vertically adjustable carriage carried by said frame,
 right and left ear engagement means removably carried on said carriage,
 adjustable lower support means for raising or lowering the head of the patient so that the patient's ear canals are aligned with said ear engagement means,
 a lower head support band removably carried by said lower support means,
 an upper support band extending across the front of the patient's face,
 nasion engagement means carried by said upper support band,
 nasion alignment means for aligning the patient's nasion with said nasion engagement means,
 pressure application means for applying a predetermined force to said ear engagement and nasion engagement means, and
 means for securing said engagement means under pressure to form a unitary headband.

5. The apparatus of claim 4 further comprising:
 mounting means carried by said medical equipment, and;
 alignment means for precisely and repeatably aligning said ear engagement means in said mounting means.

* * * * *